US007761152B2

(12) United States Patent
Chen et al.

(10) Patent No.: US 7,761,152 B2
(45) Date of Patent: Jul. 20, 2010

(54) DELAY TO THERAPY FOLLOWING CONTROLLED ATRIAL SHOCK THERAPY REQUEST

(75) Inventors: Victor T. Chen, Minnetrista, MN (US); Gary T. Seim, Minneapolis, MN (US); Carlos Ricci, Apple Valley, MN (US); Michael L. Favet, Vadnais Heights, MN (US); Hal Propp, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 221 days.

(21) Appl. No.: 11/273,980

(22) Filed: Nov. 15, 2005

(65) Prior Publication Data
US 2006/0079939 A1 Apr. 13, 2006

Related U.S. Application Data

(63) Continuation of application No. 10/643,513, filed on Aug. 19, 2003, now Pat. No. 7,024,240, which is a continuation of application No. 09/839,123, filed on Apr. 20, 2001, now Pat. No. 6,618,617.

(51) Int. Cl.
*A61N 1/39* (2006.01)
(52) U.S. Cl. .............................. 607/5; 607/60
(58) Field of Classification Search ................ None
See application file for complete search history.

(56) References Cited

U.S. PATENT DOCUMENTS 3,952,750 A * 4/1976 Mirowski et al. ............. 607/5
4,344,437 A * 8/1982 Markowitz ................. 607/9
4,421,114 A * 12/1983 Berkovits et al. ........... 607/14
5,311,449 A 5/1994 Adams
5,336,245 A 8/1994 Adams et al.
5,342,408 A 8/1994 deCoriolis et al.
5,464,431 A * 11/1995 Adams et al. ............... 607/4
5,490,862 A 2/1996 Adams et al.
5,518,001 A 5/1996 Snell
5,662,689 A * 9/1997 Elsberry et al. ............. 607/5
5,674,249 A 10/1997 de Coriolis et al.
5,755,737 A 5/1998 Prieve et al.

(Continued)

OTHER PUBLICATIONS

*Medtronic Jewel AF Model 7250 System Reference Guide*, Minneapolis, Minnesota, (1997), pp. 3-11 through 3-12 and 7-11 through 7-13.

*Primary Examiner*—Carl H. Layno
*Assistant Examiner*—Jon-Eric C. Morales
(74) *Attorney, Agent, or Firm*—Schwegman, Lundberg, Woessner, P.A.

(57) ABSTRACT

An implantable cardiac device detects a patient therapy request originating from external to the implantable device. A shock therapy delay period is timed in response to the detection of the patient therapy request. Atrial shock therapy is provided to the patient after expiration of the shock therapy delay period (if the presence of an ongoing atrial arrhythmia is detected). The patient therapy request may be provided by a patient activator including a magnet for operating a reed switch in the implanted device to provide the request. A patient activator including an input and receiver/transmitter circuitry may be employed to request the immediate providing of atrial shock therapy, and/or to set the duration the shock therapy delay period. By allowing specific delays to therapy after a therapy request, a patient can prepare for the requested therapy and thereby mitigate therapy discomfort.

17 Claims, 3 Drawing Sheets

U.S. PATENT DOCUMENTS

| | | |
|---|---|---|
| 5,775,737 A | 7/1998 | Morgner et al. |
| 5,836,975 A * | 11/1998 | DeGroot ........................ 607/5 |
| 5,999,851 A | 12/1999 | White |
| 6,016,442 A | 1/2000 | Hsu et al. |
| 6,068,651 A | 5/2000 | Brandell |
| 6,453,195 B1 * | 9/2002 | Thompson ..................... 607/3 |
| 6,618,617 B2 | 9/2003 | Chen et al. |
| 6,718,198 B2 | 4/2004 | Conley et al. |
| 2002/0156504 A1 | 10/2002 | Chen et al. |
| 2004/0034389 A1 | 2/2004 | Chen et al. |

* cited by examiner

DELAY TO THERAPY FOLLOWING CONTROLLED ATRIAL SHOCK THERAPY REQUEST

CROSS-REFERENCE TO RELATED APPLICATION(S)

This application is a continuation of U.S. patent Ser. No. 10/643,513, filed on Aug. 19, 2003, now issued as U.S. Pat. No. 7,024,240, which is a continuation of U.S. patent Ser. No. 09/839,123, filed on Apr. 20, 2001, now issued as U.S. Pat. No. 6,618,617, the specifications of which are incorporated herein by reference.

FIELD OF THE INVENTION

The present invention pertains generally to medical devices and more particularly to implantable medical devices such as devices for monitoring activity of the heart and providing electrical shock therapy thereto including automatic implantable cardioverter defibrillator devices for treating atrial arrhythmias and external patient operable devices for controlling the operation of such implantable medical devices.

BACKGROUND OF THE INVENTION

Various types of medical devices are employed to monitor electrical or other activity of the heart and to provide therapy to the heart in response to the detection of irregular cardiac rhythms. Such devices may be implantable beneath the skin of a patient, i.e., in the patient's chest. Such implantable devices include a hermetically sealed canister containing electronic circuitry for implementing the functions of the device, one or more electrodes implanted in one or more of the chambers of the heart, or in close proximity thereto, and leads for connecting the electrodes to the circuitry within the device canister. The device circuitry includes circuitry for detecting electrical signals produced by the heart, which signals are picked up at the electrodes, along with circuitry, typically implemented in a microprocessor, for analyzing the thus-detected cardiac signals. The device may also include circuitry for providing therapy in the form of electric shock signals applied to the heart. Such signals are provided to the heart, via the leads and electrodes mounted in the heart, in response to the detection of an irregular cardiac rhythm by the analysis circuitry based on the detected cardiac activity signals. The implantable device may also include a transmitter/receiver, for transmitting cardiac activity and other information to an external device for, e.g., storage and/or further analysis, and for receiving information, such as programming instructions, from the external device via, for example, an RF link.

An example of such an implantable cardiac device is an automatic implantable cardioverter defibrillator (AICD) for treating atrial arrhythmias, e.g., atrial tachycardia, fibrillation, flutter, etc. (The functionality of an atrial AICD may be combined with those of a bradycardia pacemaker, ventricular defibrillator, etc., in a single implantable device.) Atrial arrhythmias are probably the most common cardiac arrhythmia. Although atrial arrhythmias are not usually life-threatening, patients with atrial arrhythmias generally experience palpitations of the heart, and may experience dizziness or even loss of consciousness. Atrial arrhythmias, such as atrial fibrillation, also have been associated with strokes and other conditions. Atrial arrhythmias can occur suddenly. Implantable atrial cardioverter defibrillators are programmed to detect the onset of atrial arrhythmias and to provide an appropriate electrical shock therapy to the atria to terminate the atrial arrhythmia. The atrial shock therapy to be provided may depend upon the type of atrial arrhythmia detected, e.g., atrial tachycardia versus atrial fibrillation. Shock therapy provided by an implantable atrial cardioverter defibrillator may include a relatively high voltage level atrial defibrillation or cardioversion pulse, which is typically delivered to the atria in synchronism with a detected or paced ventricular activation, to terminate atrial fibrillation or flutter. Atrial antitachycardia pacing may be applied by the implantable device to terminate atrial tachycardia. Atrial antitachycardia pacing typically involves a train of pacing pulses applied to the atria at a rate slightly higher than the rate of the tachycardia.

Various systems and methods have been developed to allow patients having implanted atrial cardioverter defibrillators to monitor and control, to at least some degree, operation of the implanted device. For example, U.S. Pat. No. 5,490,862 describes an implantable atrial defibrillator which may be programmed to operate in a patient activated mode of operation. In the patient activated mode, an atrial fibrillation intervention sequence is performed by the implanted device in response to the receipt of a sequence command generated from external to the patient. The sequence command may be generated, for example, by an external magnet applied by the patient to near the implantation site, to close and then open a reed switch mounted in the implanted device and coupled to the device microprocessor. The intervention sequence thus initiated by the patient, when he believes he is experiencing an atrial arrhythmia, includes atrial fibrillation detection by the implanted device and, if atrial fibrillation is confirmed, the application of cardioverting electrical energy to the atria.

U.S. Pat. No. 5,674,249 describes the use of a portable communication device which allows a patient to monitor and control the operation of an implanted atrial defibrillator. The portable communication device, which may be dimensioned to be hand held by a patient, includes a transmitter/receiver for communicating with the implanted device via a telemetry (e.g., RF) link. In this system, an atrial fibrillation intervention sequence may be initiated in an implanted device in response to a sequence command generated from the portable communication device. The patient may also use the portable communication device to program the implanted device into an automatic mode, wherein the intervention sequence is initiated automatically at predetermined times. The handheld portable communication device receives an acknowledgment signal from the implanted device when a command signal sent from the communication device is received by the implanted device. The receipt of the acknowledgment signal by the portable handheld communication device is displayed to the patient on the device. The display includes a description of the task being performed by the implanted device in response to the command signal sent by the patient. Thus, a patient is able both to monitor and control operation of an implanted cardiac device to some degree.

U.S. Pat. No. 5,999,851 describes an implantable atrial defibrillator which includes an atrial fibrillation detection only mode of operation. In this mode, atrial fibrillation detection is initiated in the implanted device by a command signal sent from an external patient operated communication device, which is in communication with the implanted defibrillator via a telemetry (e.g., RF) link. If atrial fibrillation is detected by the implanted atrial defibrillator, an appropriate signal is communicated to the patient operated communication device, and a visual and/or audible message is provided by the communication device to the patient to indicate whether or not atrial fibrillation is detected. In this detection only mode, a further signal must be provided from the communication device to the implanted device to initiate cardioversion therapy, preferably after continued atrial fibrillation is confirmed by the implanted device.

In each of the systems described above, atrial fibrillation detection, or atrial fibrillation detection followed by atrial shock therapy, if required, may be initiated by a patient using an external communication device. In each case, where atrial shock therapy is requested by the patient, shock therapy is delivered by the implanted device immediately after it is requested by the patient (perhaps after a slight delay to confirm the presence of an atrial arrhythmia and to synchronize the atrial shock therapy delivery to a ventricular activation). The delivery of shock therapy to a patient's heart can cause great discomfort to the patient. If shock therapy is delivered essentially immediately following a patient's request, the patient's ability to prepare for the therapy or to mitigate the discomfort of the therapy before therapy delivery is severely limited. For example, a patient may wish to take analgesics or a sedative, lie down, or take other measures, such as begin exercises (calisthenics), or go to sleep, to mitigate shock perception before atrial shock therapy is provided by an implanted device. Current systems, in which patient requested atrial shock therapy is provided essentially immediately following a therapy request, do not allow patients to make many of these preparations. It would be difficult for a patient to simultaneously exercise and request atrial shock therapy using a conventional system for patient requested shock therapy, if the patient wished to reduce shock perception using exercise. Similarly, it would be impossible for a patient to go to sleep and then initiate an atrial shock therapy request using a conventional system.

What is desired, therefore, is a system which allows a patient to control the providing of atrial shock therapy by an implanted device and in which the providing of therapy is delayed by a specific delay period after shock therapy is requested. The therapy delay period is preferably long enough for the patient to prepare for the application of shock therapy (e.g., by exercise, sleep, etc.) after a shock therapy request is made. Preferably, a patient is also able to adjust the therapy delay period and select whether shock therapy will be provided immediately upon request or after expiration of the delay period.

SUMMARY OF THE INVENTION

The present invention provides a system and method which allows a patient with an implanted automatic implantable cardioverter defibrillator to delay the providing of shock therapy to the atria by the implanted device in response to a patient request for shock therapy. In accordance with the present invention, a patient employs an external activator communication device to request therapy from an implanted device. A shock therapy delay period is timed by the implanted device in response to the patient therapy request. An appropriate atrial shock therapy is provided by the implanted device after expiration of the shock therapy delay period (preferably after confirmation of an ongoing atrial arrhythmia). The patient may be allowed to select the therapy delay period, and/or to select whether patient requested atrial shock therapy is provided by the implanted device immediately following a therapy request or after expiration of the shock therapy delay period.

The present invention may be implemented in an implantable cardiac device, such as an automatic implantable cardioverter defibrillator, which provides atrial arrhythmia detection and electrical shock therapy to the atria to terminate such atrial arrhythmias. (The implantable device may also provide ventricular arrhythmia monitoring and ventricular shock therapy functionality and/or ventricular pacing functionality, as well as atrial pacing capability.) The implantable cardiac device includes signal detection circuitry, connected via leads to electrodes positioned in the atria and, preferably, the ventricles of the heart, to detect electrical heart activity signals. An implanted device system processor monitors the output provided by the signal detection circuitry to detect the occurrence of an atrial arrhythmia, e.g., atrial tachycardia, fibrillation, and/or flutter, using known atrial arrhythmia detection algorithms. The implantable device includes cardioverter/defibrillator circuitry, controlled by the device processor, for providing defibrillation shock therapy, and/or antitachycardia pacing, depending upon the type of atrial arrhythmia identified, to the atria via the leads and electrodes implanted in the heart. The implantable device is preferably also provided with a telemetry receiver/transmitter, coupled to the device processor, to allow the processor to transmit cardiac activity and other data to an external programmer device for storage and/or further analysis, and to receive data, such as programming instructions, from the external programmer device. (The external programmer device is a relatively complicated device used by a physician to program the implanted device and query cardiac activity data therefrom.)

In accordance with the present invention, a patient, having an implanted cardiac device in accordance with the present invention, is able to control the providing of atrial shock therapy by the implanted device using a patient activator communication device. The patient activator is preferably a relatively small, handheld device, which allows the patient to send a patient therapy request to the implanted device to control the providing of shock therapy to the atria by the implanted device to terminate an atrial arrhythmia event. The patient activator preferably employs a relatively simple mechanism for providing a patient therapy request. For example, the patient activator may include a magnet which, when placed near the implantation site of the implanted device, operates a reed switch in the implanted device, which is coupled to the implanted device processor, thereby to provide a patient therapy request to the implanted device.

In response to the receipt of a patient therapy request, the implanted device begins timing a shock therapy delay time period. The shock therapy delay time period may be pre-programmed by a physician, using an external programmer device, or programmed by the patient using a more sophisticated patient activator device. The delay time period is preferably selected to be sufficiently long so as to allow a patient sufficient time to prepare for and/or mitigate the discomfort of atrial shock therapy to be delivered to the patient in response to the atrial shock therapy request. The shock therapy delay time period may thus be set from several minutes (to allow a patient time to take an analgesic or sedative, to lie down, or to begin exercising) to several hours (to allow a patient to go to sleep after requesting therapy so that shock therapy is provided at night during sleep). After the shock therapy delay time period has expired, an appropriate atrial shock therapy is provided by the implanted device. Preferably, such atrial shock therapy is provided only after confirmation by the implanted device of an ongoing atrial arrhythmia event.

The patient activator communication device may also be employed to control an implanted cardiac device withhold completely the providing of atrial shock therapy by the device. For example, a patient therapy request may only be detected by the implanted device if a patient therapy request signal is maintained for longer than a therapy request signal threshold duration, e.g., by maintaining a patient activator device magnet in position to operate the reed switch in the implanted device for more than the threshold duration. In such a case, the delay time period may be timed in response to removal of the patient therapy request signal (e.g., removal of the patient activator from the implant site) and an appropriate shock therapy (e.g., synchronized cardioversion and/or antitachycardia pacing, depending upon the nature of the atrial arrhythmia) provided by the implanted device after expiration of the delay time period and confirmation of an ongoing atrial arrhythmia. If the patient activator device is removed from near the implantation site shortly after it is applied (i.e., within less than the therapy request signal threshold duration from initial application of the activator to the implantation site), atrial shock therapy will be withheld (i.e., disabled), and no atrial shock therapy will be provided even though an atrial arrhythmia, has been detected and atrial shock therapy is otherwise available. If the providing of atrial shock therapy is withheld in this manner, the patient may use the activator communication device to initiate delayed patient requested atrial shock therapy at a later time which is more convenient or appropriate for the patient.

Although a relatively simple and inexpensive patient activator device, e.g., including a magnet, may be employed in accordance with the present invention, a more complicated patient activator may also be used. A more complicated patient activator communication device may include a receiver/transmitter for communicating control signals to the implanted cardiac device via a telemetry (e.g., RF) link with a corresponding receiver/transmitter in the implanted device. Such a patient activator communication device may include a patient input circuit, including buttons, switches, etc., for allowing a patient to signal via the telemetry link from the activator to the implanted device a patient therapy request. A patient may employ such a patient activator communication device to provide different types of therapy requests to the implanted device to request either immediate atrial shock therapy, or delayed shock therapy, as described above. For example, using such an activator device, a patient therapy delay request may be provided by the patient to the implanted device. In response to receipt of the patient therapy delay request, shock therapy is provided by the implanted device after timing a shock therapy delay period (after the delay period expires and an ongoing atrial arrhythmia is confirmed). In contrast, atrial shock therapy may be provided to the patient by the implanted device immediately following receipt of a patient therapy request from the activator in which no therapy delay is requested. Such a patient activator may also be employed by the patient to provide a shock therapy delay period setting command to the implanted device, thereby to set the shock therapy delay period to a time period desired by the patient.

Further objects, features, and advantages of the invention will be apparent from the following detailed description taken in conjunction with the accompanying drawings.

DETAILED DESCRIPTION OF THE INVENTION

Figure 1:
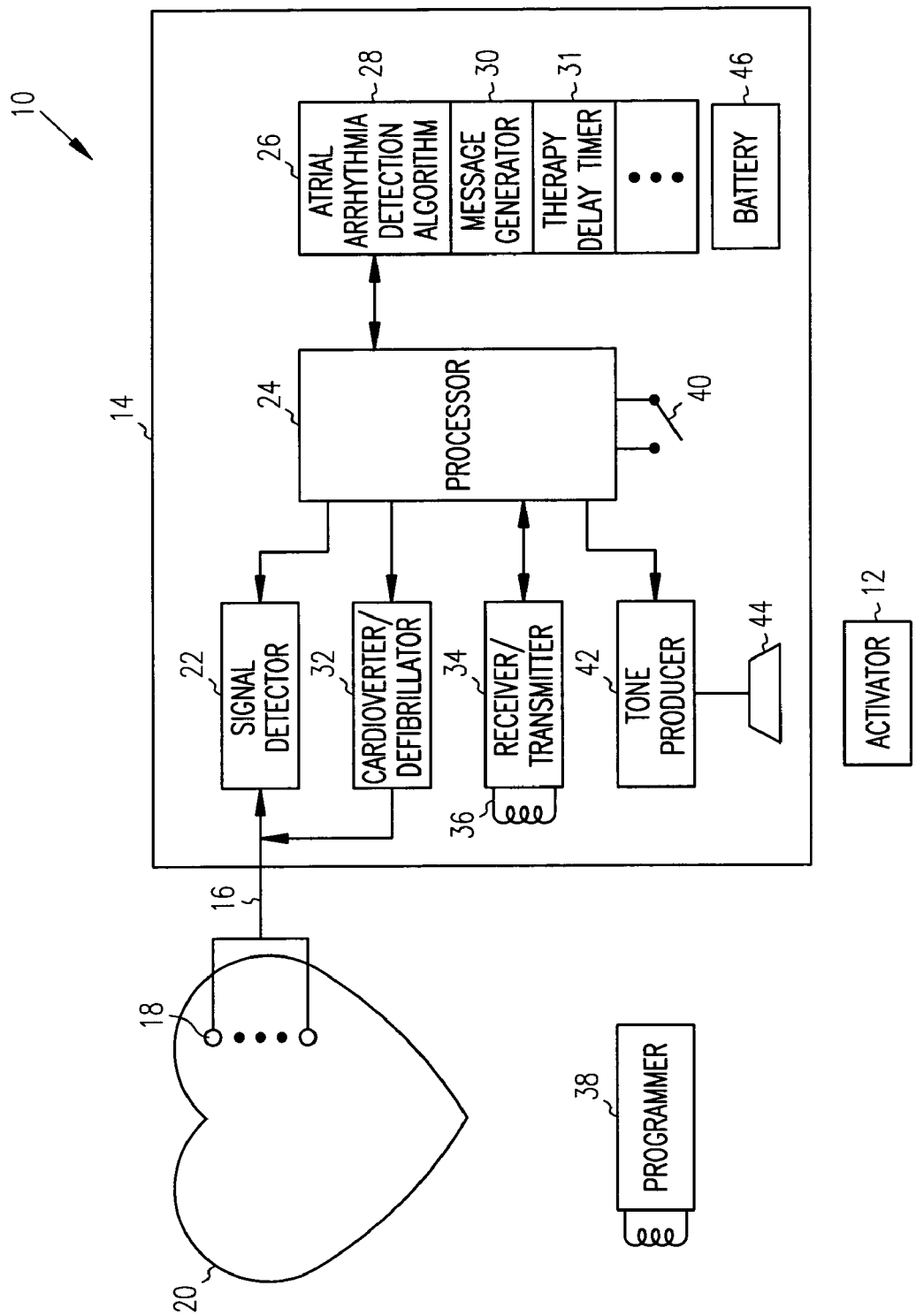
FIG. 1 is a schematic diagram of an exemplary implantable cardiac device for detecting atrial arrhythmias and providing electrical shock therapy to the atria, and a patient activator communication device for controlling the implantable device to provide atrial shock therapy after expiration of a delay time period in accordance with the present invention.

An exemplary implantable cardiac device 10 which may be controlled by a patient activator communication device 12 to provide delayed patient controlled atrial shock therapy in accordance with the present invention is illustrated in, and will be described in detail with reference to, FIG. 1. Although described in detail herein with reference to an implantable device 10 having the primary function of detecting and treating atrial arrhythmias, it should be understood that the present invention may be employed with an implantable device which also performs other functions, such as ventricular monitoring and therapy and single or dual chamber bradycardia pacing.

The implantable cardiac device 10 includes a hermetically sealed canister 14 which encloses circuitry for detecting and analyzing cardiac arrhythmias and for providing electrical shock therapy to treat such arrhythmias. The circuitry within the canister 14 is connected via one or more leads 16 to one or more electrodes 18 which are implanted in or near the chambers of a patient's heart 20. The electrodes 18 pick up electrical signals produced in the chambers of the heart 20 and provide electrical contact for electrical pulses or shocks which are delivered to the chambers of the heart 20 to pace or defibrillate/cardiovert the heart 20. Depending upon the specific applications and functionality of the implantable cardiac device 10, electrodes 18 may be positioned in or near the atria, ventricles, or, preferably, both the atria and ventricles of the heart 20. In an implantable cardiac device 10 in accordance with the present invention for detecting atrial arrhythmias, and providing atrial shock therapy to terminate such atrial arrhythmias, for example, electrodes 18 are positioned in or near the atrial, for detecting atria activity and providing atrial shock therapy to the atria, as well as in the ventricles, for detecting ventricular activity, e.g., for use in verifying the presence of atrial arrhythmias and in synchronizing the providing of atrial cardioversion shock pulses to the atria with ventricular events. A plurality of leads 16 may be required to connect the electrodes 18 positioned in the heart 20 to the circuitry within the device canister 14. As is known in the art, multiple electrodes 18 may be coupled to the circuitry within the canister 14 via a single one of the leads 16. The canister 14, leads 16, and electrodes 18 are preferably designed such that the entire device 10 is implantable beneath the skin of a patient.

The leads 16 connect the electrodes 18 positioned within the heart 20 to signal detection circuitry 22 within the implantable device canister 14. The signal detection circuitry 22 may be implemented in a conventional manner to provide atrial and/or ventricular activity signals based on the cardiac signals picked up at the electrodes 18. Conventional signal detection circuitry 22 may include signal amplifiers and filters, and may include, in addition, circuitry for detecting atrial and ventricular depolarizations and for providing atrial and ventricular depolarization detection indication signals in response thereto, along with circuitry for obtaining electrogram signals and for providing digitized electrograms from the cardiac signals detected at the electrodes 18.

The signals provided by the signal detection circuitry 22 are provided to an implantable device system processor 24. The system processor 24 may be implemented, for example, as one or more conventional microprocessors with associated memory 26. Memory 26 may be an integral part of, or separated from, but coupled to, the processor 24. Memory 26 is employed in a conventional manner to store data, such as cardiac activity data, for analysis by the processor 24, well as to store the programming instructions which control the functions performed by the processor 24. For example, programming instructions for implementing an atrial arrhythmia detection algorithm 28 by the processor 24, for operating the processor 24 to generate messages 30 for indicating the receipt of a patient therapy request from the patient activator communication device 12, and for timing time periods such as a therapy delay period 31, etc., may be stored in memory 24. These functions will be described in more detail below. Of course, other general and conventional programming instructions for the processor 24 may also be stored in memory 26.

The implantable cardiac device 10 also includes conventional cardioverter/defibrillator circuitry 32 for applying electrical energy to the heart 20 via the leads 16 and electrodes 18 positioned in the heart. In response to the detection of an atrial arrhythmia by the processor 24, based on cardiac signals provided by the signal detector 22, the processor 24 controls the cardioverter/defibrillator 32 to provide electrical shock therapy to the heart 20 to terminate the atrial arrhythmia event. The type of electrical shock therapy provided to the heart 20 may depend upon the type of atrial arrhythmia event identified. For example, the cardioverter/defibrillator circuitry 32 may be controlled by the processor 24 to provide a relatively high voltage level atrial defibrillation pulse to the atria of the heart 20 to terminate an atrial fibrillation or flutter event. Such relatively high voltage shock therapy is preferably provided in synchronism with a detected or paced ventricular event, in order to prevent the atrial shock therapy from initiating a more serious ventricular arrhythmia. In response to the detection of a high-rate, but more regular, atrial arrhythmia, e.g., atrial tachycardia, the processor 24 may control the cardioverter/defibrillator circuitry 32 to provide atrial anti-tachycardia pacing to the atria to terminate the atrial arrhythmia event. Atrial antitachycardia pacing may typically include a rapid series of atrial pacing pulses delivered to the atria via a pacing lead 16 and one or more electrodes 18 positioned in or near the atria of the heart 20. Various atrial shock therapies are known to those skilled in the art, and will not be described in further detail herein. As discussed above, atrial shock therapy, especially atrial defibrillation shock therapy, can be very uncomfortable for the patient receiving it. Such discomfort can be mitigated by the patient, however, such as by taking an analgesic or sedative before therapy is provided, or by exercising during the delivery of atrial shock therapy.

The implantable device 10 may include receiver/transmitter circuitry 34 including an antenna coil 36. The receiver/transmitter 34 may be implemented in a conventional manner to transmit data from the system processor 24 out of the implanted device 10 to a remote programmer device 38. For example, cardiac activity data detected by the signal detector circuitry 22 may be transmitted to the external programmer device 38 to be stored and analyzed therein in more detail than is possible in the implanted device 10 itself. The receiver/transmitter 34 may also receive programming instructions from the external programmer device 38 for, for example, programming operating parameters of the implantable cardiac device 10. Communication between the receiver/transmitter 34 and the external programmer device 38 may be implemented in a conventional manner, e.g., via a telemetry (e.g., RF) link. It is noted that the external programmer device 38 is a relatively large and sophisticated device which is typically employed by a physician to monitor and control operation of the implantable device 10.

In accordance with the present invention, the implantable cardiac device 10 may also include a reed switch 40 mounted therein and coupled to the system processor 24. As will be discussed in more detail below, the reed switch 40 is operated (closed or opened) by the application of a magnetic field near the site of implantation in a patient of the implantable cardiac device 10. The system processor 24 detects the operation of the reed switch 40 as a patient therapy request. In response to the patient therapy request, the system processor 24 initiates timing of a therapy delay period. After expiration of the therapy delay period, the system processor 24 controls the cardioverter/defibrillator 32 to deliver atrial shock therapy to the heart 20 of the patient, preferably after confirming the presence of an ongoing atrial arrhythmia.

In accordance with the present invention, the implantable cardiac device 10 may preferably also include tone generation circuitry 42. The tone generation circuitry 42 may be implemented in a conventional manner, and is controlled by the system processor 24 to drive a small speaker 44 to produce tones of sufficient volume to be audible by a patient in which the implantable device 10 is implanted. As will be discussed in more detail below, the tones produced by the tone general circuitry 42 and speaker 44 may be used to indicate to a patient that a patient therapy request has been received by the implanted device 10 from the patient activator communication device 12.

The implantable cardiac device 10 also includes a battery 46, which provides power for the processor 24 and other circuit components of the implantable cardiac device 10.

The circuitry for implementing the signal detector 22, processor 24, cardioverter/defibrillator 32, receiver/transmitter 34, tone producer 42, and other functions of the implantable cardiac device 10 may be implemented in a conventional manner using analog or digital circuitry, including one or more microprocessors, or any combination thereof. As will be known to those skilled in the art, functions performed by the signal detector 22, cardioverter/defibrillator 32, receiver/transmitter 34, and tone producer 42, may be performed by independent analog and/or digital circuitry, as suggested by the illustration of FIG. 1, or may be implemented in one or more processors 24, or with a combination of independent circuits and one or more processors.

In accordance with the present invention, a patient in which the implantable cardiac device 10 is implanted may employ a patient activator communication device 12 to request the delayed providing of atrial shock therapy by the implanted device 10. The patient activator 12 preferably designed to be portable, and is preferably small in size and able to be held easily in the hand and manipulated by a patient. Various components which may be implemented in an activator 12 in accordance with the present invention are illustrated schematically in FIG. 2.

The activator 12 may preferably include a magnet 48 mounted therein. (In its simplest form, a patient activator 12 in accordance with the present invention may be implemented with a magnet 48 alone). When the patient activator 12 is positioned near the implant site of the implantable device 10, the magnetic field generated by the magnet 48 in the activator 12 operates the reed switch 40 coupled to the processor 24 in the implantable device 10. Operation of the reed switch 40 in this manner for at least a minimal period of time, e.g., two seconds, is detected by the implanted device processor 24 as a patient therapy request which initiates the timing of a shock therapy delay period by the processor 24, followed by the providing of atrial shock therapy. The processor 24 may preferably employ the message generator function 30 to generate a message which is provided to the patient to indicate that the patient therapy request has been received by the implanted device. Such a message may be provided to the patient, as described above, by controlling tone generation circuitry 42 in the implantable device 10 to generate a tone audible to the patient to indicate that the patient therapy request has been received and that the requested and appropriate action will be taken by the implantable device 10 in response thereto.

The message generated by the implantable device 10 to indicate that a patient therapy request, or other command, has been received thereby may also preferably be provided in a visual form to the patient, e.g., in a visual display provided on the patient activator 12. For example, the activator 12 may include tone detection circuitry 50. The tone detection circuitry 50 may be implemented in a conventional manner to detect the tones produced by the tone generation circuitry 42 in the implantable cardiac device 10, and to generate electrical signals in response thereto. The electrical signals generated by the tone detection circuitry 50 in the activator 12 may be provided to an activator processor 52, which decodes the signals provided by the tone detection circuitry 50. The activator 12 also includes conventional display circuitry 54. The display circuitry 54 may be driven by the activator processor 52, in response to the signals received from the tone detection circuitry 50, to provide a visual indication to the patient confirming receipt of a patient therapy request by the implantable cardiac device 10. For example, the display circuitry 54 may include one or more LEDs or lamps 56 which are illuminated in a conventional manner to indicate, e.g., that a patient therapy request has been received by the implanted device 10 from the activator 12.

Figure 2:
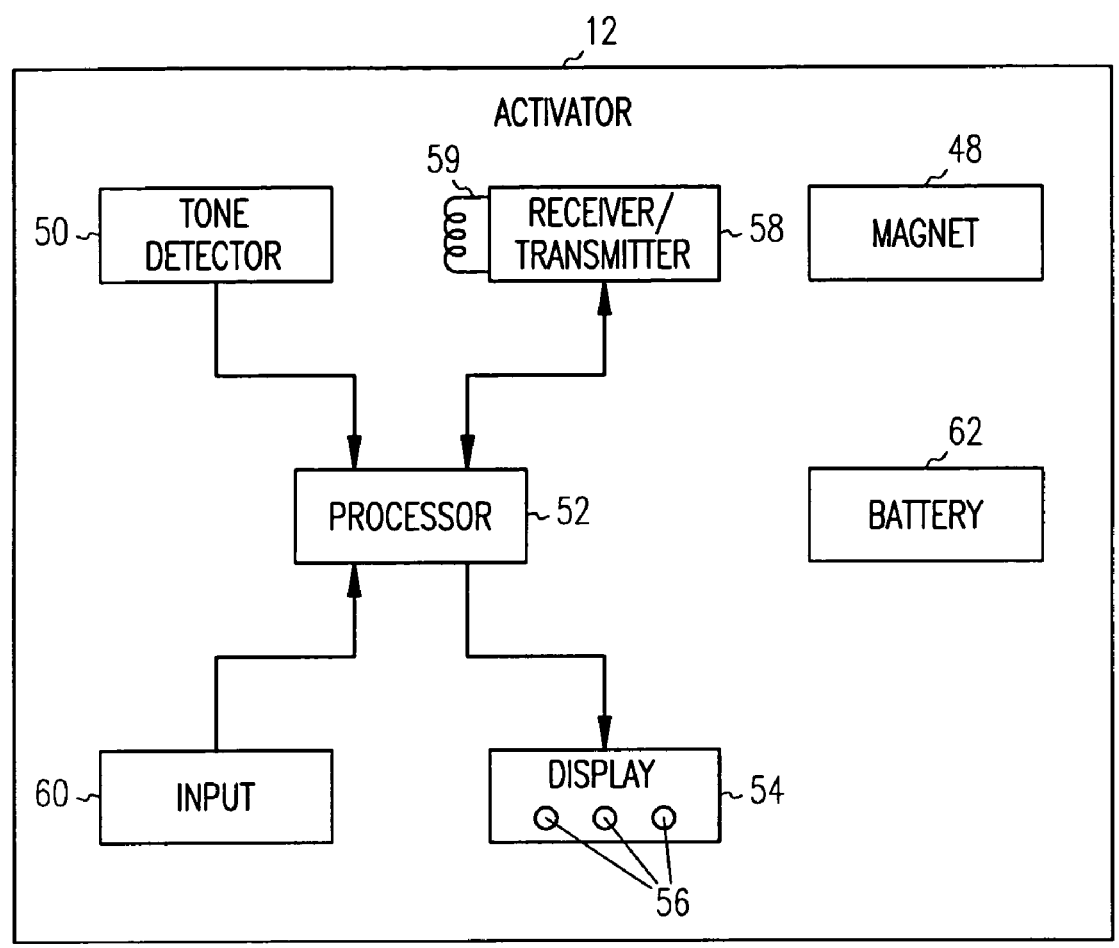
FIG. 2 is a more detailed schematic diagram of an exemplary patient activator communication device which may be used to request delayed atrial shock therapy in accordance with the present invention.

As an alternative to the magnet 48, for providing a patient therapy request to the implanted cardiac device 10, and tone detector circuitry 50, for detecting an audible message indicating that a therapy request has been received by the implanted device 10, the activator 12 may include conventional receiver/transmitter circuitry 58, including an antenna 59. The activator receiver/transmitter 58 may be implemented in a conventional manner, and may be coupled to the receiver/transmitter 34 (or another similar circuit) in the implanted device 10, via a telemetry (e.g., RF) link, to both provide patient therapy request signals to and receive confirmation of the receipt of such requests from the implanted cardiac device 10. The activator receiver/transmitter 58 may be coupled to, and controlled by, the activator processor 52. Patient input circuitry 60 is preferably also provided in the activator 12 and coupled to the activator processor 52. The activator input circuitry 60 may include conventional buttons, switches, dials, etc., and related electronic circuitry. A patient employs the activator input circuitry 60 to initiate patient therapy request. For example, the patient may push a button on the activator 12, which is part of the input circuitry 60, to request the delayed providing of atrial shock therapy by the implanted device 10. A signal generated by the activator input circuitry 60 is received by the processor 52 which, in turn, generates a command signal requesting, e.g., the delayed providing of atrial shock therapy by the implanted device 10. This command signal is, in turn, provided to the activator receiver/transmitter 58, to be transmitted to the implanted device 10, e.g., via the receiver/transmitter 34 therein, over the telemetry link. The received command signal is, in turn, processed by the implanted device processor 24. In response to the request, a message indicating, e.g., that the patient therapy request has been received, is generated by the implanted device processor 24, and provided to the implanted device receiver/transmitter 34 for transmission back to the activator 12. This confirmation message is received by the activator receiver/transmitter 58 and provided to the activator processor 52. The activator processor 52 processes the confirmation message received from the implanted device 10, and generates therefrom an indication that a patient therapy request has been received by the implanted device 10, which, e.g., may be presented to the patient by controlling the activator display 54. Of course, the confirmation indication may be provided visually, audibly, and/or in any other manner to a patient on the activator 12. The activator input 60 and receiver/transmitter circuitry 58 may also be employed to request immediate, rather than delayed, atrial shock therapy from the implanted device 10, to instruct the implanted device to withhold the providing of atrial shock therapy, and/or to allow the patient to set the shock therapy delay period, as will be described in more detail below. It should be noted that a patient activator 12 will typically include either the receiver/transmitter 58 and input circuitry 60 or a magnet 48 and tone detector 50, but may include both systems, as illustrated in FIG. 2.

An exemplary process in accordance with the present invention for controlling an implanted cardiac device 10 to provide delayed atrial shock therapy following a patient controlled atrial shock therapy request will now be described in detail with reference to the exemplary flowchart diagram of FIG. 3. In accordance with the present invention, as discussed above, a patient employs a patient activator 12, implemented using either a magnet 48 for operating a reed switch 40 in the implanted device 10, or an input circuit 60 and receiver/transmitter 58 forming a telemetry link with the implanted device 10, to provide a patient therapy request to the implanted device 10. A patient therapy request provided by the patient using the activator 12 and detected by the implanted device 10 controls the implanted device 10 to provide delayed atrial shock therapy, giving the patient sufficient time to prepare for receipt of the therapy, to mitigate therapy discomfort. As will be discussed in more detail below, the patient therapy request may also be used to control the implanted device 10 to withhold entirely the providing of atrial shock therapy, which may be enabled at a later time by the patient, and/or to request the immediate delivery of atrial shock therapy by the implanted device 10, without a delay. Each of these options is considered in the exemplary flowchart diagram of FIG. 3. It should be understood, however, that an implantable patient controllable atrial shock therapy device in accordance with the present invention need not provide each and every one of these patient control options. The ability of a patient to control the implantable device 10 in any manner to be described herein may be enabled or disabled, e.g., by a physician. This may be achieved by programming the implanted device 10, e.g., using the external programmer device 38.

Figure 3:
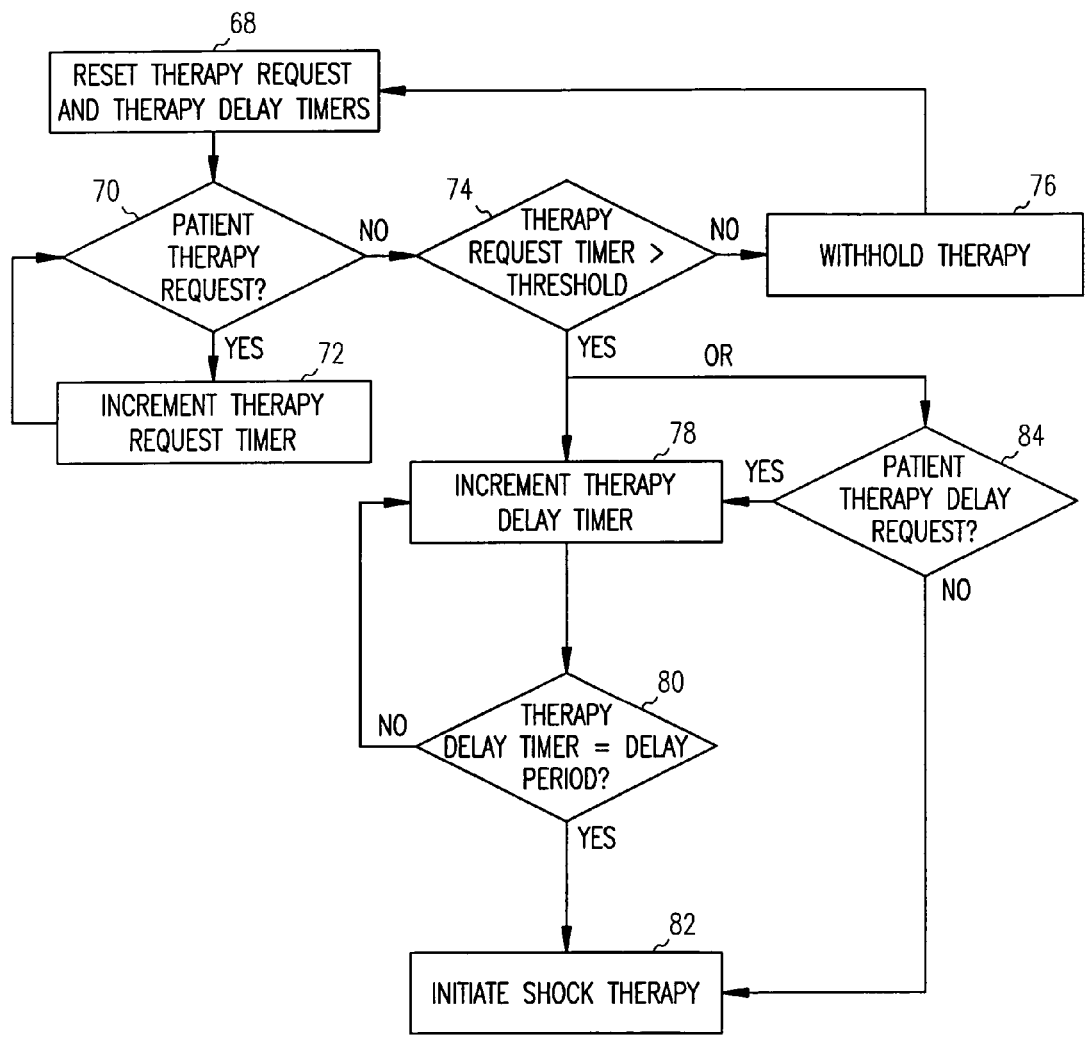
FIG. 3 is flowchart diagram illustrating an exemplary method for requesting delayed atrial shock therapy from an implanted cardiac device in accordance with the present invention using a patient activator communication device.

The exemplary process illustrated in FIG. 3 employs two timers. A therapy request timer is employed to time the duration of the presence of an activator magnet 48 near the implant site of the implanted device 10. Thus, the therapy request timer is employed to time the duration of operation of the reed switch 40 in the implanted device 10 by the magnet 48. As will be described in more detail below, use of the therapy request timer allows a patient to use a simple activator device 12 including magnet 48 to request either the delivery of delayed atrial shock therapy by the implanted device 10 or to withhold the providing of atrial shock therapy by the implanted device 10. The therapy delay time 31 is employed to time the therapy delay period in response to detection of patient therapy request. Atrial shock therapy may be delivered by the implanted device 10 to the patient after expiration of the therapy delay period. Both the therapy request and therapy delay timers may be implemented in or controlled by the implanted device processor 24 and may, of course, be either up or down timers. The therapy request and therapy delay timers are initially reset at step 68.

The implanted device processor 24 continually detects for the receipt of a patient therapy request originating from external to the implantable device 10 at 70. As discussed above, the patient therapy request may be provided by positioning an activator magnet 48 near the implant site of the implantable device 10, to operate the reed switch 40 in the implantable device 10. If a patient therapy request is detected in this manner, the therapy request timer is incremented at 72 as long as the patient therapy request, e.g., operation of the reed switch 40, is detected. When the patient therapy request is no longer detected, e.g., when the activator magnet 48 is removed from near the implant site of the implantable device 10, the implanted device processor 24 compares at 74 the current value of the therapy request timer to a therapy request signal threshold duration. This threshold duration may be programmable, and may be, for example, approximately seven seconds. If the value of the therapy request timer indicates that the activator magnet 48 was only in position to operate the reed switch 40 for less than the therapy request signal threshold duration, the implanted device 10 may be instructed to withhold the providing of atrial shock therapy at 76. If the implanted device 10 is thus instructed to withhold the providing of atrial shock therapy, the therapy request timer is reset at 68 and the implanted device processor 24 continues to detect for the next patient therapy request at 70. Thus, by employing the patient activator magnet 48 to provide the patient therapy request signal for less than a therapy request signal threshold duration, a patient may control the implanted device 10 to withhold the providing of atrial shock therapy until the patient again uses the activator 12 to request specifically the providing of delayed (or immediate) atrial shock therapy by the implanted device 10.

If the patient therapy request is provided for longer than the therapy request signal threshold duration, i.e., if the therapy request timer is determined at 74 to have a value greater than the threshold value, the providing of delayed atrial shock therapy by the implanted device 10 is requested. If the providing of delayed atrial shock therapy is requested, the therapy delay timer 31 is incremented at 78 and checked at 80 to determine if the value of the therapy delay timer equals the selected therapy delay period. The function of these steps 78 and 80 is, therefore, to time a shock therapy delay period following and in response to receipt of a patient therapy request by the implanted device 10. The therapy delay period may be preprogrammed by a physician, using the programmer device 38, or selectable by a patient, as will be discussed in more detail below. The therapy delay period is preferably selected to be sufficiently long so as to allow a patient to prepare for the requested atrial shock therapy after such a request is made. This allows a patient to take action to mitigate therapy discomfort by, e.g., taking analgesics or sedatives, lying down, or taking other measures, such as exercising to mitigate shock perception. The shock therapy delay period may be set to a duration of minutes to several hours. A shock therapy delay period of several hours would allow a patient, for example, to employ the activator 12 to request delayed atrial shock therapy before going to sleep in the evening, thereby delaying shock therapy for a sufficient duration such that the implantable device 10 provides atrial therapy shocks at night during the patient's sleep.

After expiration of the shock therapy delay period, the implantable device 10 initiates atrial shock therapy at 82. The step of initiating atrial shock therapy 82 may preferably include confirmation of the ongoing presence of an atrial arrhythmia by the implanted device processor 24 using, e.g., conventional atrial arrhythmia detection algorithms 28. If an atrial arrhythmia is confirmed, the processor 24 may control the cardioverter/defibrillator 32 to provide an appropriate atrial shock therapy to the patient's heart 20 to terminate the atrial arrhythmia detected. As discussed above, atrial shock therapy may involve the application of a relatively high voltage level atrial defibrillation pulse to the patient's heart 20, preferably in synchronism with a detected or paced ventricular activation, to terminate atrial fibrillation or flutter, or a train of atrial antitachycardia pacing pulses, to terminate a high rate but more regular atrial tachycardia.

Where the patient employs a patient activator 12 which includes input 60 and receiver/transmitter circuitry 58 for providing command signals to the implanted device 10 over a telemetry link, specific instructions may be selected by the patient, using the input circuit 60, and provided to the implanted device 10 over the telemetry link, to either request or withhold the providing of atrial shock therapy. Thus, if such an activator device 12 is employed, there may be no need to employ the therapy request timer, as described above. Using such an activator device 12, a patient may also be enabled to provide a patient therapy request signal to the implanted device 10 in response to which atrial shock therapy is provided to the patient immediately (following the confirmation of an ongoing atrial arrhythmia) rather than following the timing of a shock therapy delay period. For example, at step 84 (FIG. 3) the implantable device processor 24 may determine whether the patient therapy request telemetered from the activator 12 is a request for the providing of immediate atrial shock therapy or delayed atrial shock therapy. If a patient therapy delay request is indicated, the implanted device processor 24 begins timing the shock therapy delay period 78, 80, after the expiration of which shock therapy is initiated 82. In contrast, if the patient therapy request telemetered from the activator 12 does not indicate a request for the providing of delayed atrial shock therapy, the implanted device processor 24 initiates the providing of atrial shock therapy at 82 immediately, without first timing the shock therapy delay period.

A patient activator 12 in accordance with the present invention which includes input 60 and receiver/transmitter circuitry 58 may also be employed by a patient to set the shock therapy delay period, the period between the receipt of a patient therapy request from the patient by the implanted device 10 and the delivery of atrial shock therapy to the patient by the implanted device 10, to a desired shock therapy delay period duration. For example, the patient may employ the input circuitry 60 to select a desired shock therapy delay period duration. In response, a shock therapy delay period setting command, indicating the desired shock therapy delay period, is generated by the activator processor 52 and transmitted from the activator 12 via the receiver/transmitter 58 to the implanted device 10. In response to receipt of the telemetered shock therapy delay period setting command, the implanted device processor 24 sets the shock therapy delay period to the desired delay period selected by the patient. Thus, a patient may be allowed both to control and specify the amount of delay to therapy following a patient therapy request.

It should be understood that the present invention is not limited to the particular exemplary embodiments and applications thereof illustrated and described herein, but embraces such modified forms thereof as come within the scope of the following claims. In particular, it should be understood that not all of the steps illustrated schematically in FIG. 3 need be performed, and the steps illustrated may be performed in a different order, in accordance with the present invention.

What is claimed is:

1. An implantable device for providing atrial shock therapy controllable by a patient using an external activator, the implantable device comprising:
   an atrial arrhythmia detector to detect an atrial arrhythmia;
   an atrial cardioverter/defibrillator to provide an atrial shock;
   a receiver/transmitter to receive a patient therapy request and a delay period from the external activator via a telemetry link; and
   a processor adapted to time the delay period between receipt of the patient therapy request by the receiver/transmitter and providing the atrial shock and control the atrial cardioverter/defibrillator to provide the atrial shock upon expiration of the delay period in response to the patient therapy request being a request for a delayed atrial shock therapy, and to control the atrial cardioverter/defibrillator to provide the atrial shock, without timing the delay period, in response to the patient therapy request being a request for an immediate atrial shock therapy.

2. The implantable device of claim 1, wherein the processor is adapted to generate a confirmation message indicating that the patient therapy request has been received.

3. The implantable device of claim 2, wherein the receiver/transmitter is adapted to transmit the confirmation message to the external activator.

4. The implantable device of claim 2, further comprising tone generation circuitry and a speaker to produce a tone indicating that the patient therapy request has been received, the tone audible by the patient.

5. The implantable device of claim 1, wherein the processor is adapted to confirm a presence of the atrial arrhythmia before the providing of the atrial shock.

6. The implantable device of claim 1, wherein the telemetry link comprises an RF telemetry link.

7. A system for patient controllable atrial shock therapy, the system comprising:
   an implantable device including:
      a signal detector to provide cardiac activity signals;
      an atrial cardioverter/defibrillator to deliver an atrial shock;
      an implantable device processor, coupled to the signal detector and the atrial cardioverter/defibrillator, to control the delivery of the atrial shock in response to a patient therapy request, the implantable device processor adapted to time a delay period upon receipt of the patient therapy request and initiate a delivery of the atrial shock upon expiration of the delay period in response to the patient therapy request being a request for a delayed atrial shock therapy, and to initiate the delivery of the atrial shock, without timing the delay period, in response to the patient therapy request being a request for an immediate atrial shock therapy; and
      an implantable device receiver/transmitter to receive the patient therapy request and the delay period via a telemetry link; and
   an external patient activator including:
      patient input circuitry to receive the patient therapy request and the delay period; and
      an activator receiver/transmitter to transmit the patient therapy request and the delay period to the implantable device receiver/transmitter via the telemetry link.

8. The system of claim 7, wherein the implantable device further comprises a message generator coupled to the implantable device processor, the message generator adapted to generate a confirmation message confirming receipt of the patient therapy request.

9. The system of claim 8, wherein the external patient activator further comprises a display, coupled to the activator processor, to present a visual indication confirming the receipt of the patient therapy request by the implantable device.

10. The system of claim 9, wherein the patient input circuitry is adapted to receive a request for withholding the delivery of the electrical energy.

11. A method for operating an implantable cardiac device, the method comprising:
   detecting an atrial arrhythmia using the implantable cardiac device;
   receiving an external patient therapy request and a delay period transmitted from an external activator to the implantable cardiac device via a telemetry link;
   timing the delay period and providing an atrial shock upon expiration of the delay period in response to the patient therapy request being a request for a delayed atrial shock therapy; and
   providing the atrial shock, without timing the delay period, in response to the patient therapy request being a request for an immediate atrial shock therapy.

12. The method of claim 11, further comprising confirming a presence of the atrial arrhythmia before the providing of the atrial shock therapy.

13. The method of claim 11, further comprising generating a confirmation message indicating the receipt of the patient therapy request by the implantable cardiac device.

14. The method of claim 13, further comprising presenting an audible tone using a speaker of the implantable cardiac device, the audible tone indicating the receipt of the patient therapy request by the implantable cardiac device.

15. The method of claim 13, further comprising:
   transmitting the confirmation message from the implantable cardiac device to the external activator; and
   presenting the confirmation message visually using the external activator.

16. The method of claim 11, wherein receiving the external patient therapy request signal transmitted from the external activator to the implantable cardiac device via the telemetry link comprises receiving the external patient therapy request signal transmitted from the external activator to the implantable cardiac device via an RF telemetry link.

17. The method of claim 16, further comprising receiving an external patient request for withholding the providing of the atrial shock during the delay period.

* * * * *

UNITED STATES PATENT AND TRADEMARK OFFICE
CERTIFICATE OF CORRECTION

PATENT NO. : 7,761,152 B2
APPLICATION NO. : 11/273980
DATED : July 20, 2010
INVENTOR(S) : Victor T. Chen et al.

It is certified that error appears in the above-identified patent and that said Letters Patent is hereby corrected as shown below:

On the Title page, in field (54), in "Title", in column 1, line 1, after "FOLLOWING" insert -- PATIENT --.

In column 1, line 1, after "FOLLOWING" insert -- PATIENT --.

Signed and Sealed this

Twelfth Day of October, 2010

David J. Kappos
*Director of the United States Patent and Trademark Office*